United States Patent [19]

Köppe et al.

[11] 4,010,158

[45] Mar. 1, 1977

[54] 1-(2'-ETHYNYL-PHENOXY)-2-HYDROXY-3-BUTYLAMINO-PROPANES AND SALTS

[75] Inventors: Herbert Köppe; Karl Zeile; Werner Kummer; Helmut Stahle, all of Ingelheim am Rhein; Albrecht Engelhardt, Mainz (Rhine), all of Germany

[73] Assignee: Boehringer Ingelheim GmbH, Ingelheim am Rhein, Germany

[22] Filed: Jan. 18, 1973

[21] Appl. No.: 324,844

Related U.S. Application Data

[63] Continuation-in-part of Ser. No. 727,078, May 6, 1968, abandoned.

[30] Foreign Application Priority Data

May 18, 1967 Germany .............................. 92594

[52] U.S. Cl. ........................... 260/253; 260/348 R; 260/501.17; 260/501.19; 260/570.7; 260/612 D; 424/253; 424/316; 424/330
[51] Int. Cl.² ............... C07C 93/06; C07D 473/00
[58] Field of Search .......... 260/570.7, 253, 501.17, 260/501.15; 424/330

[56] References Cited

UNITED STATES PATENTS

| | | | |
|---|---|---|---|
| 3,203,992 | 8/1965 | Kunz et al. | 260/570.7 |
| 3,590,084 | 6/1971 | Peperkamp | 260/570.7 |

*Primary Examiner*—Robert V. Hines
*Attorney, Agent, or Firm*—Hammond & Littell

[57] ABSTRACT

Compounds of the formula

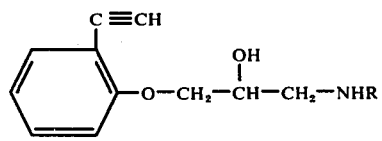

wherein R is secondary butyl or tertiary butyl, and their non-toxic, pharmacologically acceptable acid addition salts; the compounds as well as their salts are useful as β-adrenergic receptor blocking agents and hypotensives.

3 Claims, No Drawings

1-(2'-ETHYNYL-PHENOXY)-2-HYDROXY-3-BUTYLAMINO-PROPANES AND SALTS

This is a continuation-in-part of copending application Ser. No. 727,078, filed May 6, 1968 now abandoned.

This invention relates to novel 1-(ethynyl-phenoxy)-2-hydroxy-3-butylamino-propanes and acid addition salts thereof, as well as to a method of preparing these compounds.

More particularly, the present invention relates to compounds of the formula

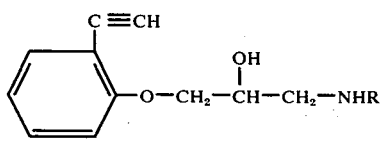

wherein R is secondary butyl or tertiary butyl, and their non-toxic, pharmacologically acceptable acid addition salts.

The compounds embraced by formula I above may be prepared by reacting a compound of the formula

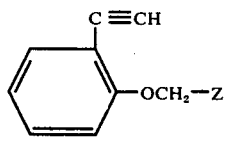

wherein Z is

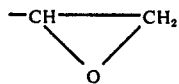

or —CHOH-CH$_2$Hal, where Hal is halogen, with an amine of the formula

    III.

wherein R has the same meanings as in formula I.

The epoxide of the formula II may readily be prepared by reacting a compound of the formula

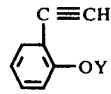

wherein Y is hydrogen or a cation, such as an alkali metal ion, with epichlorohydrin in alkaline solution. The phenol of the formula IV (Y = H) may itself be prepared according to the method described in Bull. Chem. Soc. (Japan) 29 (1956), pages 471 (reported in Chem. Abstr. 51, page 8705b). It may be converted into the corresponding phenolates (Y = alkali metal ion) by treatment with aqueous alkalis.

The epoxide of the formula II may be used for the preparation of the halohydrin of the formula II by addition of the corresponding hydrogen halide.

The amines embraced by formula III are known compounds.

The compounds of the formula I according to the invention possess an asymmetric carbon atom in the —CHOH— grouping and occur therefore in form of racemates as well as optically active antipodes. The optically active compounds may be obtained either by starting from the corresponding optically active starting compounds. If they exist, or by converting the racemates into diasteromeric salts in conventional manner, for instance, by means of ditoluyl tartaric acid, dibenzoyl tartaric acid or 3-bromocamphor-8-sulfonic acid, and separating the diastereomeric salts by means of fractional crystallization.

The compounds embraced by formula I above are organic bases and therefore form acid addition salts with inorganic or organic acids. Examples of non-toxic, pharmacologically acceptable acid addition salts include, but are not limited to, those formed with hydrochloric acid, hydrobromic acid, sulfuric acid, methanesulfonic acid, maleic acetic, acetic acid, oxalic acid, lactic acid, tartaric acid, 8-chlorotheophylline or the like. Such acid addition salts may be formed by conventional methods, such as by dissolving the free base in a suitable solvent and acidifying the solution with the desired acid.

The following examples further illustrate the present invention and will enable others skilled in the art to understand it more completely.

EXAMPLE 1

1-(2-ethynyl-phenoxy)-2-hydroxy-3-tert.butylaminopropane and its hydrochloride 12 gm (0.07 mol) of 1-(2'-ethynyl-phenoxy)-2,3-epoxy-propane were dissolved in 100 ml of methanol, and 18 gm (0.25 mol) of tert.butylamine were added to the solution. The mixture was allowed to stand overnight at room temperature and was then heated at 60° C for 2 hours. Thereafter, the methanol was distilled off in vacuo, the residue was dissolved in dilute HCl, and the solution was filtered through activated charcoal. The clear aqueous filtrate was made alkaline with NaOH, the precipitated basic components were taken up in ether, the ethereal phase was dried over MgSO$_4$, and the ether was distilled off. The oily residue, 1-(2'-ethynyl-phenoxy)-2-hydroxy-3-tert.butylaminopropane, was dissolved in ethanol, and by addition of ethereal HCl the hydrochloride was precipitated. After isolation of the crystallizate, it was recrystallized twice from ethanol by addition of ether, whereupon it had a melting point of 172°–174° C.

EXAMPLE 2

1-(2'-Ethynyl-phenoxy)-2-hydroxy-3-sec.butylaminopropane and its hydrochloride 13.8 gm of raw 1-(2'-ethynyl-phenoxy)-2,3-epoxypropane, obtained from 10.4 gm (0.088 mol) of 2-ethynyl-phenol and 8.8 gm (0.095 mol) of epichlorohydrin, were dissolved in 120 cc of ethanol, 22 gm (0.3 mol) of sec.butylamine were added to the solution, and the mixture was refluxed for 2 hours. Thereafter, the ethanol was distilled off in vacuo, the residue was stirred with dilute hydrochloric acid, the acid aqueous solution was extracted with ether, and the aqueous phase was made alkaline with sodium hydroxide. The oily precipitate formed thereby was taken up in ether, the ethereal solution was washed with water and then dried over magnesium sulfate, and the ether was distilled off. The solid residue was recrystallized from ethyl acetate and petroleum ether, yielding the free base 1-(2'-ethynyl-phenoxy)-2-hydroxy-3-sec.butylamino-propane. The base was dissolved in ethanol, the solution was acidified with ethereal hydrochloric acid, and the precipitate formed thereby was collected. 7.4 gm of 1-(2'-ethynyl-phenoxy)-2-hydroxy-3-sec.butylamino-propane hydrochloride, m.p. 149°–151° C, were obtained.

The compounds according to the present invention, that is, racemic mixtures of the compounds embraced by formula I, the optically active antipode components thereof, and the non-toxic, pharmacologically acceptable acid addition salts of said racemic mixtures of optically active antipodes, have useful pharmacodynamic properties. More particularly, the compounds of the present invention exhibit $\beta$-adrenolytic and hypotensive activities in warm-blooded animals, such as guinea pigs and mice. By "$\beta$-adrenolytic" we mean an inhibiting effect upon adrenergic $\beta$-receptors. Thus, the compounds of the present invention are useful for the treatment of coronary and/or circulatory disorders, particularly cardiac arrhythmia and tachycardia, in warm-blooded animals.

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective single dosage unit of the compounds according to the present invention is from 0.002 to 5 mgm/kg, preferably 0.25 to 1.66 mgm/kg for oral administration, and 0.002 to 0.40 mgm/kg for parenteral administration.

The following examples illustrate a few dosage unit compositions comprising a compound of the instant invention as an active ingredient and represent the best mode contemplated of putting the invention into practical use. The parts are parts by weight unless otherwise specified.

EXAMPLE 3

Tablets

The tablet composition was compounded from the following ingredients:

| | |
|---|---|
| 1-(2'-ethynyl-phenoxy)-2-hydroxy-3-tert.butylamino-propane . HCl | 30.0 parts |
| Corn starch | 179.0 parts |
| Secondary calcium phosphate | 240.0 parts |
| Magnesium stearate | 1.0 parts |
| Total | 450.0 parts |

Compounding procedure

The individual ingredients were intimately mixed, and the mixture was granulated in the conventional way. The granulate was pressed into 450 mgm-tablets. Each tablet contained 30 mgm of the propane compound and, when administered perorally to a warm-blooded animal of about 60 kg body weight in need of such treatment, produced very good $\beta$-adrenolytic effects.

EXAMPLE 4

Gelatin Capsules

The capsule filler composition was compounded from the following ingredients:

| | |
|---|---|
| 1-(2'-ethynyl-phenoxy)-2-hydroxy-3-sec.butylamino-propane . HCl | 35.0 parts |
| Corn starch | 165.0 parts |
| Total | 200.0 parts |

Compounding procedure

The ingredients were intimately admixed, and 200 mgm portions of the mixture were filled into gelatin capsules of suitable size. Each capsule contained 35 mgm of the propane compound and, when administered perorally to a warm-blooded animal of about 60 kg body weight in need of such treatment, produced very good $\beta$-adrenolytic effects.

EXAMPLE 5

Coated Sustained-release Pills

The pill core composition was compounded from the following ingredients:

| | |
|---|---|
| 1-(2'-ethynyl-phenoxy)-2-hydroxy-3-sec.butylamino-propane . HCl | 40.0 parts |
| Carboxymethyl cellulose (CMC) | 300.0 parts |
| Stearic acid | 20.0 parts |
| Cellulose acetate phtalate (CAP) | 40.0 parts |
| Total | 400.0 parts |

Compounding procedure

The propane compound, the CMC and the stearic acid were intimately admixed, and the mixture was granulated in the conventional way, using a solution of the CAP in 200 ml of a mixture of ethanol and ethylacetate. Then, the granulate was pressed into 380 mgm-pill cores, which were coated in the customary manner with a sugary 5% solution of the polyvinylpyrrolidone in water. Each coated pill contained 25 mgm of the propane compound and, when administered perorally to a warm-blooded animal of about 60 kg body weight in need of such treatment, produced very good $\beta$-adrenolytic effects.

EXAMPLE 6

Hypodermic Solution

The solution was compounded from the following ingredients:

| | |
|---|---|
| 1-(2'-ethynyl-phenoxy)-2-hydroxy-3-tert.butylamino-propane . HCl | 2.5 parts |
| Sodium salt of EDTA (ethylene-diamine-tetra acetic acid) | 0.2 parts |
| Distilled water | 100.0 parts by vol. |

Compounding procedure

The active ingredient and the EDTA salt were dissolved in a sufficient quantity of distilled water, and the solution was diluted to the desired volume with additional distilled water. The solution was filtered until free from suspended particles and filled into 1 cc-ampules under aseptic conditions. Finally the ampules are sterilized and sealed. Each ampule contained 25 mgm of the propane compound, and when the contents thereof were administered intravenously to warm-blooded animal of about 60 kg body weight, very good $\beta$-adrenolytic effects were produced.

A dosage unit composition comprising a compound of the present invention as an active ingredient may also comprise one or more other active ingredients, such as cardiac-active or circulatory-active sympathomimetics or coronary dilators, as illustrated by the following example.

EXAMPLE 7

Tablets

The tablet composition was compounded from the following ingredients:

| | |
|---|---|
| 1-(2'-ethynyl-phenoxy)-2-hydroxy-3-tert.butylamino-propane . HCl | 30.0 parts |
| 2,6-Bis(diethanolamino)-4,8-dipiperidino-pyrimido[5,4-d]pyrimidine | 75.0 parts |
| Lactose | 169.0 parts |
| Corn starch | 194.0 parts |
| Colloidal silicic acid | 14.0 parts |
| Polyvinylpyrrolidone | 6.0 parts |
| Magnesium stearate | 2.0 parts |
| Soluble starch | 10.0 parts |
| Total | 500.0 parts |

The propane compound and the pyrimidopyrimidine compound were intimately admixed with the lactose, the corn starch, the colloidal silicic acid and the polyvinylpyrrolidone, and the mixture was granulated in the conventional way, using an aqueous solution of the soluble starch. The granulate was admixed with the magnesium stearate, and the mixture was pressed into 500 mgm-tablets. Each tablet contained 30 mgm of the propane compound and 75 mgm of the pyrimidopyrimidine compound and, when administered perorally to a warm-blooded animal of about 60 kg body weight in need of such treatment, produced very good $\beta$-adrenolytic and coronary dilating effects.

The amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

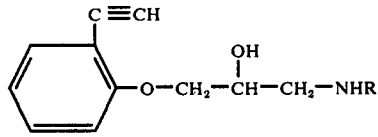

wherein R is secondary butyl or tertiary butyl, or a non-toxic, pharmacologically acceptable acid addition salt thereof.

2. A compound of claim 1, which is 1-(2'-ethynyl-phenoxy)-2-hydroxy-3-tert.butylamino-propane, or a non-toxic, pharmacologically acceptable acid addition salt thereof.

3. A compound of claim 1, which is 1-(2'-ethynyl-phenox)-2-hydroxy-3-sec.butylamino-propane, or a non-toxic, pharmacologically acceptable acid addition salt thereof.

* * * * *